United States Patent
Wang et al.

(10) Patent No.: US 10,258,669 B2
(45) Date of Patent: Apr. 16, 2019

(54) POLYPEPTIDE AND POLYPEPTIDE COMPLEX FOR SUPPRESSING TUMOR METASTASIS AND TREATING LEUKEMIA AS WELL AS PREPARATION METHOD THEREFOR AND APPLICATION THEREOF

(71) Applicants: National Center for Nanoscience and Technology, China, Beijing (CN); Institute of Basic Medical Sciences, Chinese Academy of Medical Sciences, Beijing (CN)

(72) Inventors: Chen Wang, Beijing (CN); Hongyang Duan, Beijing (CN); Yanlian Yang, Beijing (CN); Haiyan Xu, Beijing (CN); Xiaojin Li, Beijing (CN); Hua Guo, Beijing (CN); Hanyi Xie, Beijing (CN); Yue Yu, Beijing (CN)

(73) Assignees: National Center for Nanoscience and Technology, China, Beijing (CN); Institute of Basic Medical Sciences, Chinese Academy of Medical Sciences, Beijing (CN)

( * ) Notice: Subject to any disclaimer, the term of this patent is extended or adjusted under 35 U.S.C. 154(b) by 0 days.

(21) Appl. No.: 15/328,355

(22) PCT Filed: Jul. 1, 2015

(86) PCT No.: PCT/CN2015/083021
§ 371 (c)(1),
(2) Date: Apr. 24, 2017

(87) PCT Pub. No.: WO2016/011878
PCT Pub. Date: Jan. 28, 2016

(65) Prior Publication Data
US 2017/0360897 A1    Dec. 21, 2017

(30) Foreign Application Priority Data

Jul. 23, 2014   (CN) .......................... 2014 1 0353810
Sep. 25, 2014  (CN) .......................... 2014 1 0497974

(51) Int. Cl.
| | | |
|---|---|---|
| A61K 38/38 | (2006.01) |
| A61K 38/08 | (2006.01) |
| A61K 38/04 | (2006.01) |
| A61K 38/16 | (2006.01) |
| A61K 45/06 | (2006.01) |
| A61K 47/42 | (2017.01) |
| C07K 14/00 | (2006.01) |
| C07K 7/06 | (2006.01) |
| C07K 7/08 | (2006.01) |
| C07K 7/00 | (2006.01) |
| C07K 14/76 | (2006.01) |
| A61K 47/64 | (2017.01) |

(52) U.S. Cl.
CPC ............ *A61K 38/385* (2013.01); *A61K 38/08* (2013.01); *A61K 38/16* (2013.01); *A61K 47/42* (2013.01); *A61K 47/643* (2017.08); *C07K 7/06* (2013.01); *C07K 14/00* (2013.01); *A61K 45/06* (2013.01)

(58) Field of Classification Search
CPC ...... A61K 38/385; A61K 38/38; A61K 38/08; A61K 38/04; A61K 38/16; A61K 47/643; A61K 45/06; A61K 47/42; C07K 14/00; C07K 7/06; C07K 7/08; C07K 7/00; C07K 2319/31; C07K 14/76; C07K 14/765
USPC ......... 514/15.2, 19.6, 19.8, 21.5, 21.6, 21.7; 530/300, 327, 328, 363
See application file for complete search history.

(56) References Cited

U.S. PATENT DOCUMENTS

| | | | | |
|---|---|---|---|---|
| 5,876,969 | A  * | 3/1999 | Fleer ...................... | A61K 38/21 435/252.3 |
| 6,914,131 | B1 * | 7/2005 | Scarlato ................. | C07K 14/22 435/252.3 |
| 7,655,245 | B2 * | 2/2010 | Scarlato ................. | C07K 14/22 424/190.1 |
| 2004/0031072 | A1 * | 2/2004 | La Rosa ................. | C07H 21/04 800/278 |

FOREIGN PATENT DOCUMENTS

| | | |
|---|---|---|
| CN | 102002106 A | 4/2011 |
| CN | 102060913 A | 5/2011 |
| CN | 103649317 A | 3/2014 |
| CN | 104098652 A | 10/2014 |
| CN | 104231050 A | 12/2014 |

OTHER PUBLICATIONS

KORDP4_THAOC from UniProt, pp. 1-3. Integrated into UniProtKB/TrEMBL Nov. 28, 2012.*
Chen et al., "Progress on Albumin as Slightly Soluble Drugs Carrier for Injection," Chinese Journal of Pharmaceuticals, 41(1): 51-54 (2010). [Cited in Office Action in related Chinese Patent Application No. 201410353810.5, dated Dec. 31, 2015, with English Abstract].
International Search Report in International Application No. PCT/CN2015/083021, dated Jul. 1, 2015.
(Continued)

*Primary Examiner* — Julie Ha
(74) *Attorney, Agent, or Firm* — Venable LLP; Henry J. Daley; Miguel A. Lopez

(57) ABSTRACT

A group of polypeptides and a complex formed by the polypeptides and human serum albumin, a method for improving the solubility of the group of polypeptides in a salt solution by combining the polypeptides with human serum albumin, a method for preparing the complex formed by the group of polypeptides and human serum albumin, and an application of the group of polypeptides and the complex formed by the polypeptides and human serum albumin in the preparation of drugs for suppressing tumor metastasis and treating leukemia are described.

2 Claims, 15 Drawing Sheets

Specification includes a Sequence Listing.

(56) References Cited

OTHER PUBLICATIONS

Search Report dated May 30, 2018 issued in European Application No. 15824964.9.
Bikash Debnath et al., "Small Molecule Inhibitors of CXCR4", Theranostics, vol. 3, No. 1, Jan. 1, 2013 (Jan. 1, 2013), pp. 47-75, XP055391478, AU, ISSN:1838-7640, DOI: 10.1038/srep06610.
Xiaojin Li et al., "Improving chemotherapeutic efficiency in acute myeloid leukemia treatments by chemically synthesized peptide interfering with CXCR4/CXCL12 axis", Scientific Reports, vol. 5, No. 1, Dec. 1, 2015 (Dec. 1, 2015), XP055445671, DOI: 10.1038/srep16228.
Xiaojin Li et al., "A designed peptide targeting CXCR4 displays anti-acute myelocytic leukemia activity in vitro and in vivo", Scientific Reports, vol. 4, No. 1, Oct. 14, 2014 (Oct. 14, 2014), XP055445661, DOI: 10.1038/srep06610.
Hua Guo et al., "Targeting the CXCR4/CXCL12 axis with the peptide antagonist E5 to inhibit breast tumor progression", Signal Transduction and Targeted Therapy, vol. 2, Aug. 11, 2017 (Aug. 11, 2017), p. 17033, XP055475341,DOI: 10.1038/sigtrans.2017.33.
Hongyang Duan et al., "Dual-affinity peptide mediated inter-protein recognition", Organic & Biomolecular Chemistry,vol. 14, No. 48, Jan. 1, 2016 (Jan. 1, 2016), pp. 11342-11346, XP055475439,ISSN: 1477-0520, DOI: 10.1039/C60B02292H.
Meike Burger et al., "Small peptide inhibitors of the CXCR4 chemokine receptor (CD184) antagonize the activation, migration, and antiapoptotic responses of CXCL12 in chronic lymphocytic leukemia B cells", Blood, American Society of Hematology, US, vol. 106, No. 5, Sep. 1, 2005 (Sep. 1, 2005), 1824-1830, XP002629047, ISSN: 0006-4971, DOI:10.1182/Blood-2004-12-4918.
J Juarez et al., "CXCR4 antagonists mobilize childhood acute lymphoblastic leukemia cells into the peripheral blood and inhibit engraftment", Leukemia., vol. 21, No. 6, Apr. 5, 2007 (Apr. 5, 2007), pp. 1249-1257, XP055445845, US, ISSN: 0887-6924, DOI:10.1038/sj.leu.2404684.
Juarez J et al., "Effects of inhibitors of the chemokine receptor CXCR4 on acute lymphoblastic leukemia cells in vitro", Leukemia, MacMillan Press Ltd, US, vol. 17, No. 7, Jul. 1, 2003 (Jul. 1, 2003), pp. 1294-1300, XP002566663,ISSN: 0887-6924, DOI: 10.1038/SJ.LEU.2402998.
Zeng Zhihong et al., "Inhibition of CXCR4 with the novel RCP168 peptide overcomes stroma-mediated chemoresistance in chronic and acute leukemias",Molecular Cancer Therapeutics, American for Cancer Research, US, vol. 5, No. 12, Dec. 1, 2006 (Dec. 1, 2006), pp. 3113-3121, XP008139367,ISSN:1535-7163, DOI.

\* cited by examiner

SEQUENCE LISTING

<160> NUMBER OF SEQ ID NOS: 7

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1

Asn Asn Asn Asn Asn Asn Asn Asn
1               5

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Arg Ser Phe Ile Leu Leu Arg Ile Ile Gln Gly Cys Arg Arg
1               5                   10                  15

Arg Asn Thr Val Asp Asp
            20

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Arg Ser Phe Phe Leu Leu Arg Arg Ile Gln Gly Cys Arg Phe
1               5                   10                  15

Arg Asn Thr Val Asp Asp
            20

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Arg Val Ile Leu Arg Asn Gly Asp Leu Ser Arg Gly Val Thr Ile
1               5                   10                  15

Ser Tyr Asp Ser Tyr Cys Asp Asn
            20

<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Arg Arg Val Gln Phe Arg Ile Ser Ile Thr Ser Asn Asp Cys Pro
1               5                   10                  15

Asp Asp Arg Ser Arg Ser Phe Asp Ile Asp Gly
            20                  25

<210> SEQ ID NO 6
<211> LENGTH: 29
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 6

Tyr Cys Asp Asp Arg Asn Ser Ser Arg Ile Cys Ser Asn Asn Gly Arg
1               5                   10                  15

Cys Val Cys Gly Gln Cys Val Cys Asp Asp Arg Asn
            20                  25

<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Cys Val Cys Asp Asp Asp Arg Asn Thr Asn Arg Ile Tyr Ser Gly
1               5                   10                  15

Asp Phe Cys Arg Cys Arg Asn Phe Asn Cys Arg Asp Ser
            20                  25
```

POLYPEPTIDE AND POLYPEPTIDE COMPLEX FOR SUPPRESSING TUMOR METASTASIS AND TREATING LEUKEMIA AS WELL AS PREPARATION METHOD THEREFOR AND APPLICATION THEREOF

CROSS-REFERENCE OF RELATED APPLICATION

This application is a National Stage Application of PCT/CN2015/083021, filed Jul. 1, 2015, which claims priority to Chinese Patent Application No. 201410353810.5, filed Jul. 23, 2014 and Chinese Patent Application No. 201410497974.5, filed Sep. 25, 2014, the entire contents of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Jun. 19, 2017, is named 121721-411824_SequenceListing.txt and is 3,030 bytes in size.

TECHNICAL FIELD

The present invention relates to the field of biomedical technology, in particular to a polypeptide and a polypeptide complex, their preparation method and application, in particular to a polypeptide and a preparation method of a polypeptide-human serum albumin (HSA) complex capable of improving the solubility of the polypeptide in salt solution and its application in inhibiting tumor metastasis and treating leukemia.

BACKGROUND ART

Serum albumin is the most abundant protein in blood plasma, and its biological functions include binding and transporting a series of endogenous and exogenous substances as well as maintaining normal blood osmotic pressure and so on. In recent years, human serum albumin (HSA) as a drug carrier has received extensively attention. HSA consists of 585 amino acid residues, has a molecular weight of about 66 kD, and also has advantages of safety without toxicity, good biocompatibility and so on.

There are two main ways of carrying drugs by albumin: the first way is that the drug and albumin are linked by molecular chains, that is, formation of albumin-drug conjugate using chemical coupling; the second way is to rely on the interaction between drug and albumin to achieve drug embedding, that is, carrying drug by albumin using physical binding, which can improve the solubility and stability of the drug.

The current study for HSA drug carrier is mainly aimed at anti-tumor drug. Physical embedding effect of drugs carried by HSA is achieved by the physical binding of HSA, such as hydrophobic, electrostatic and other interactions to embed and carry drugs, which is capable of improving the stability and targeting ability of the drug and has sustained release effects. Therefore, HSA can be used as an ideal drug carrier for new type of complexes of peptide drugs.

Tumors are a class of diseases which impose a serious threat to people's health. Tumors can be divided into benign tumors and malignant tumors, and the main difference between the two is that the malignant tumors have characteristics of metastasis and recurrence. Tumor metastasis is a sign of poor prognosis, and is also the leading cause of death of a tumor patient.

Chemokines are a class of small single-stranded small molecular proteins that, by interaction with G-protein-coupled receptors, cause cytoskeletal rearrangement of target cells, and to adhere to endothelial cells firmly and directionally migrate. In recent years, domestic and foreign studies have showed that stromal cell-derived factor-1 (SDF-1), i.e. chemokine CXCL12, and its specific chemokine receptor CXCR4 play an important role in a variety of organ-specific metastasis of tumor. The specific chemokine receptor CXCR4 is highly expressed on the surface of many solid tumor cells and leukemic cells, while chemokine CXCL12 is highly expressed in bone marrow, lymph nodes and some organs.

Solid tumor cells and leukemic cells highly expressing CXCR4 tend to migrate to some organs such as lungs, bone marrow, etc., as origins of chemokine CXCL12 in a reverse-concentration gradient, forming organ-specific metastases (Balkwill F SeminImmunol, 2003, 15, 49-55). Therefore, targeted inhibition of CXCL12/CXCR4 interaction by using CXCR4 antagonists can block the adhesion of tumor cells and leukemia cells to stromal cells, increase the sensitivity of tumor cells and leukemic cells to chemotherapeutic drugs, and prevent the metastasis and recurrence of tumor as well as leukemia.

Since polypeptides can be easily synthesized, easily metabolized in the human body without toxic side effects and severe immune responses, it is of great importance to develop peptides specifically targeting CXCR4 receptors for inhibiting tumor metastasis and treating leukemia.

SUMMARY

The present invention aims at providing a polypeptide and a polypeptide complex, their preparation method and application, and in particular, a polypeptide with good solubility in water and poor solubility in salt and a polypeptide-HSA complex which can improve the solubility of the polypeptide in the salt solution, the preparation method thereof and the application thereof in inhibiting tumor metastasis and treating leukemia.

In order to achieve the above objects of the present invention, the present invention adopts the following technical solutions:

In the first aspect, the present invention provides a polypeptide capable of inhibiting the metastasis of tumor cells, and the polypeptide has an amino acid sequence selected from the group consisting of SEQ ID NOs: 1 to 7, as shown in Table 1.

The present invention also provides a polypeptide for inhibiting tumor cell metastasis and treating leukemia, and the polypeptide also has an amino acid sequence selected from that shown in any one of SEQ ID NOs: 1 to 7.

The polypeptide of the present invention can be prepared by artificial chemical synthesis, and has the characteristics of good solubility in water and poor solubility in salt.

As a preferable technical solution, the polypeptide has an amino acid sequence shown in SEQ ID NO: 2 or SEQ ID NO: 3, which corresponds to the names E4 and E5 in Table 1 respectively.

The polypeptide of the present invention is capable of inhibiting the migration of breast cancer cells, capable of killing leukemia cells, and prolonging the survival of mice transplanted with leukemia cells.

In a second aspect, the present invention also provides a method for improving the solubility of the polypeptide according to the first aspect of the present invention in a salt solution, the method comprising: combining the polypeptide with human serum albumin.

Preferably, the polypeptide binds to human serum albumin by physical binding.

In a third aspect, the present invention also provides a polypeptide-human serum albumin complex comprising the polypeptide according to the first aspect of the present invention and human serum albumin.

Preferably, the polypeptide binds to human serum albumin by a physical interaction.

Preferably, the molar ratio of the polypeptide to human serum albumin is 4:1-1:4, for example 4:1, 4:2, 4:3, 1:1, 1:2, 1:3, and 1:4.

In a fourth aspect, the present invention also provides a method for preparing the polypeptide-human serum albumin complex according to the third aspect of the present invention, comprising the steps of:

1) formulating the solution: formulating a solution of the polypeptide at 1-5 mg/mL, and formulating a solution of the human serum albumin at 125-250 mg/mL;

2) mixing: adding the solution of human serum albumin to the solution of the polypeptide, and mixing them well.

In the present invention, the solution of the polypeptide may be formulated at a concentration of 1-5 mg/mL, for example, at a concentration of 1 mg/mL, 1.2 mg/mL, 1.5 mg/mL, 2 mg/mL, 2.2 mg/mL, 2.5 Mg/mL, 3.5 mg/mL, 3.8 mg/mL, 4 mg/mL, 4.5 mg/mL, 5 mg/mL, preferably 2.2-4 mg/mL; the solution of the human serum albumin may be formulated at a concentration of 125-250 mg/mL, for example, at a concentration of 125 mg/mL, 130 mg/mL, 150 mg/mL, 160 mg/mL, 170 mg/mL, 180 mg/mL, 190 mg/mL, 200 mg/mL, 210 mg/mL, 220 mg/mL, 230 mg/mL, 240 mg/mL, 250 mg/mL, preferably 130-240 mg/mL.

Preferably, in step 1), both the solution of polypeptide and the solution of human serum albumin use sterile ultrapure water as a solvent.

Preferably, in step 2), the molar ratio of the polypeptide to the human serum albumin in the solution is 4:1-1:4, for example 4:1, 4:2, 4:3, 1:1, 1:2, 1:3, 1:4.

In a fifth aspect, the present invention also provides the use of the polypeptide according to the first aspect of the present invention or the polypeptide-human serum albumin complex according to the third aspect of the invention in the preparation of a medicament for inhibiting tumor cell metastasis, inhibiting tumor metastasis-related diseases or treating leukemia.

As a preferred technical solution, use of the polypeptide or polypeptide-human serum albumin complex in the preparation of a medicament for inhibiting lateral migration and/or longitudinal migration of tumor cells or leukemic cells.

As a preferable technical solution, the tumor metastasis-related disease is a tumor related to high expression of the chemokine receptor CXCR4.

Preferably, the tumor related to high expression of the chemokine receptor CXCR4 is any one of breast cancer, leukemia, lymphoma or bladder cancer, preferably but not limited to these.

Preferably, the tumors related to high expression of the chemokine receptor CXCR4 are breast cancer and leukemia.

Compared with the prior art, the invention has the following advantages:

The polypeptide-HSA complex according to the present invention has the ability to increase the solubility of a polypeptide in a salt solution. The polypeptide of the present invention has a particle size of 300 nm or more in phosphate buffer solution (PBS) at 0 h while the polypeptide-HSA complex is well dispersed in PBS solution and has a particle size of about 100 nm at 0 h, which does not change greatly within 72 h. Meanwhile, the obtained polypeptide and polypeptide-HSA complex have the effect of inhibiting tumor metastasis and treating leukemia, which can provide a feasible method and technique for inhibiting tumor metastasis and treating leukemia.

DETAILED DESCRIPTION

Figure 1A:
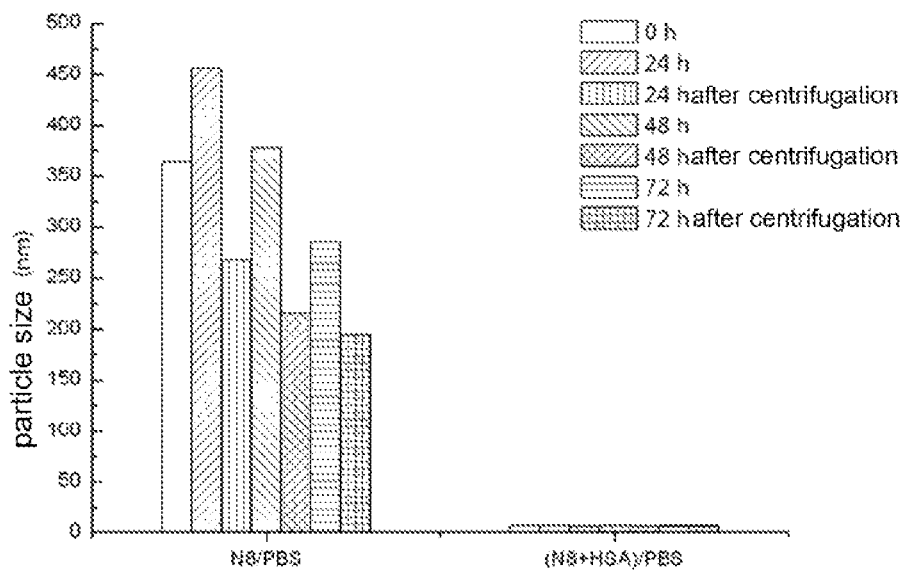
FIGS. 1a-1g are graphs showing the experimental results of dynamic light scattering of polypeptide and polypeptide-HSA complex dissolved in PBS.
Figure 1B:
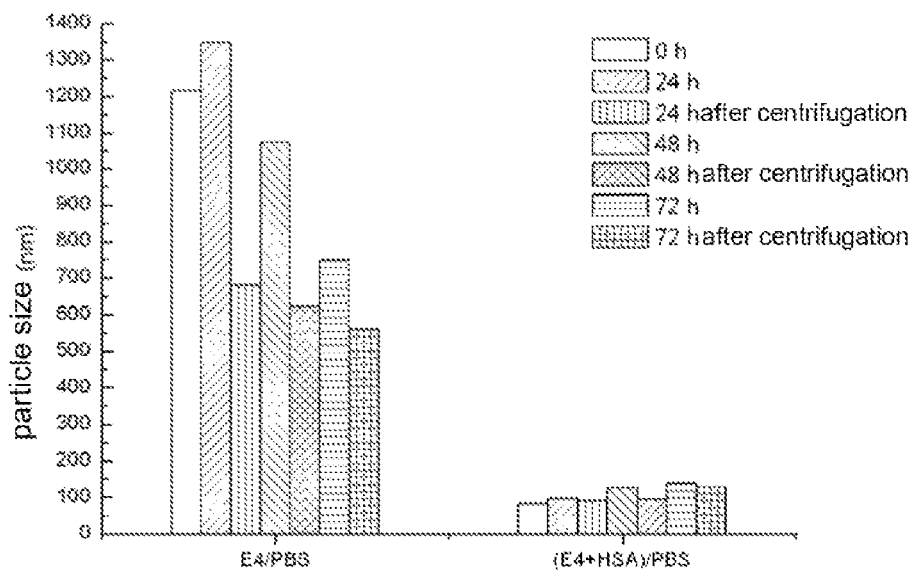
Figure 1C:
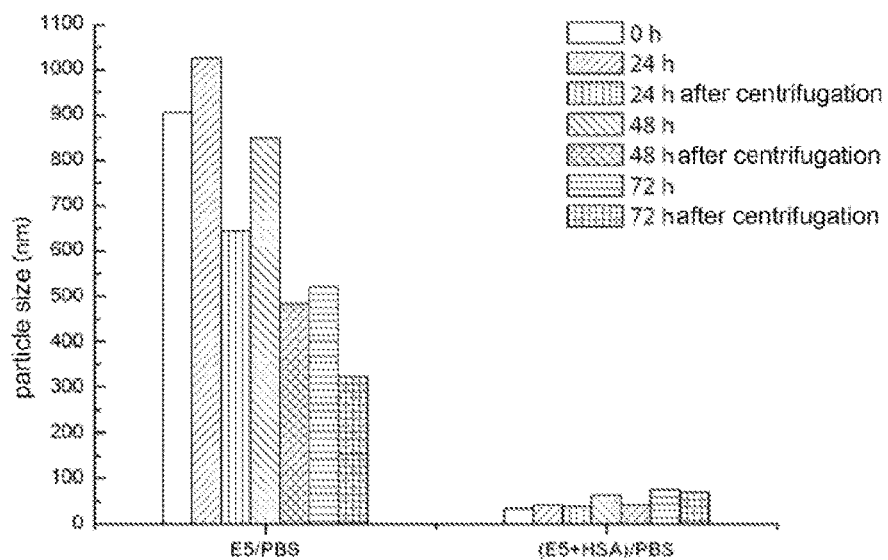
Figure 1D:
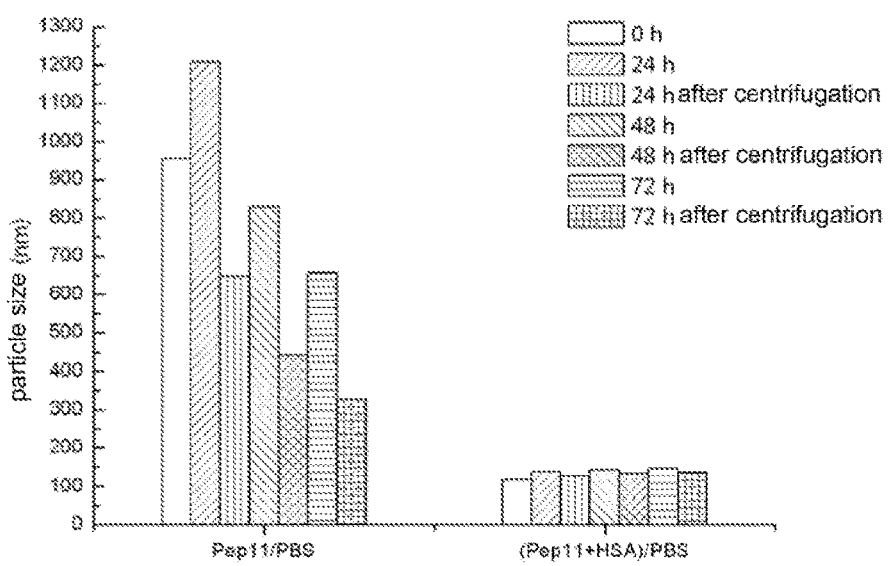
Figure 1E:
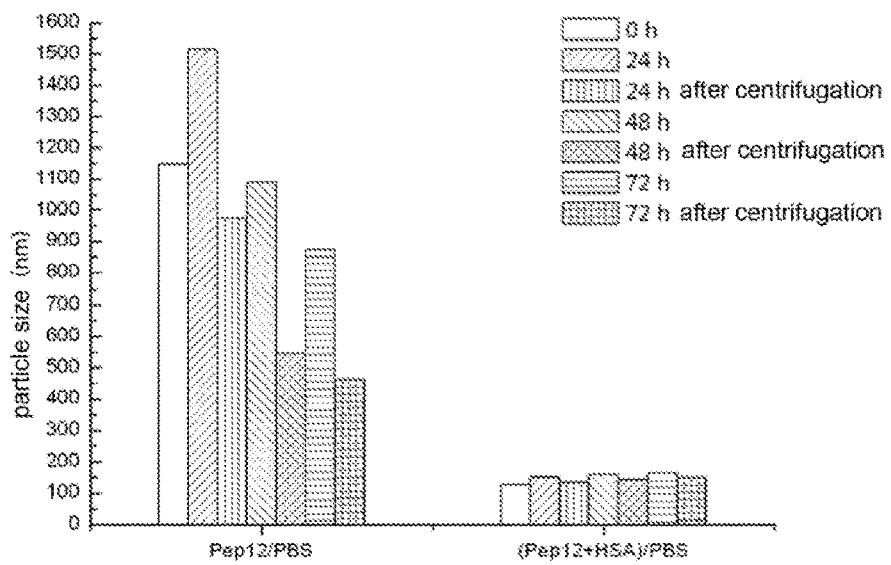
Figure 1F:
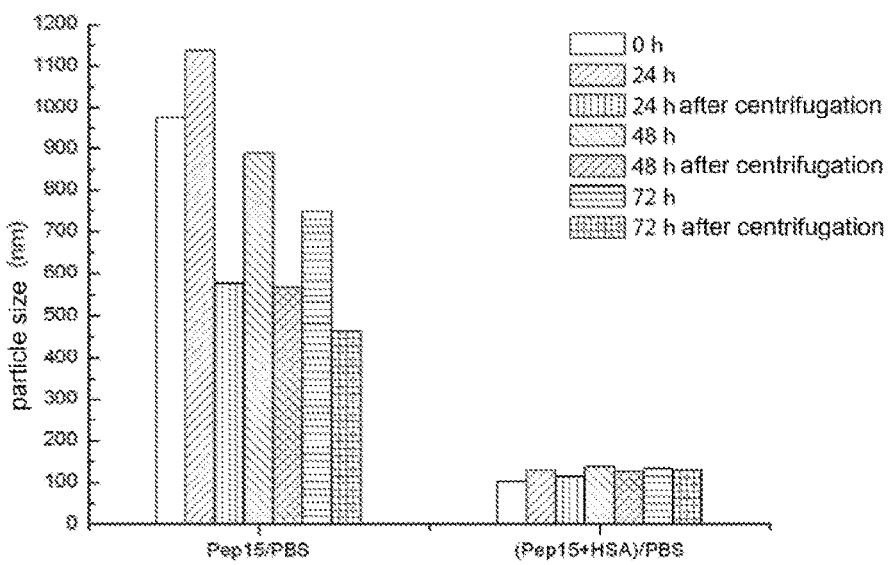
Figure 1G:
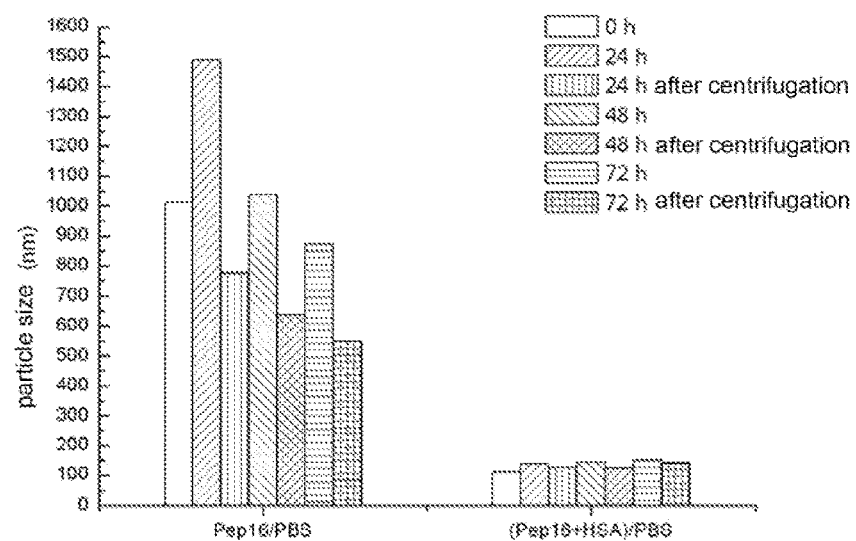

Embodiments of the present invention will be described in detail below with reference to examples. Techniques or conditions which are not specifically specified in the examples are in accordance with the techniques or conditions described in the literature in this field or the product description. The used reagents or instruments which are not specifically specified with the manufacturer are conventional products available through regular channels.

Unless otherwise specified, the breast cancer cell lines SK-BR-3, MDA-MB-231 and leukemia cell lines HL-60 and U937 used in the following examples were all purchased from the Chinese Academy of Medical Sciences.

Unless otherwise specified, the solvents of the aqueous solutions used in the following examples are sterile ultrapure water.

Unless otherwise specified, the reagents used in the following examples are all analytical grade reagents.

Unless otherwise indicated, the PBS used in the following examples are all 1×PBS.

Example 1: Synthesis of Polypeptides

The polypeptides were synthesized according to the sequences shown in Table 1 (synthesized by Shanghai Science Peptide Biological technology Co., Ltd., purity: 98%), and were respectively formulated into a mother liquor at an appropriate concentration before experiments.

TABLE 1

| name | sequence |
| --- | --- |
| N8 | NNNNNNNN (SEQ ID NO: 1) |
| E4 | Biotin-GGRSFILLRIIQGCRRRNTVDD (SEQ ID NO: 2) |
| E5 | Biotin-GGRSFFLLRRIQGCRFRNTVDD (SEQ ID NO: 3) |
| Pep11 | SRVILRNGDLSRGVTISYDSYCDN (SEQ ID NO: 4) |
| Pep12 | GRRVQFRISITSNDCPDDRSRSFDIDG (SEQ ID NO: 5) |
| Pep15 | YCDDRNSSRICSNNGRCVCGQCVCDDDRN (SEQ ID NO: 6) |
| Pep16 | QCVCDDDRNTNRIYSGDFCRCRNFNCRDS (SEQ ID NO: 7) |

The amino acid sequences of polypeptides N8, E4, E5, Pep11, Pep12, Pep15, and Pep16 correspond to SEQ ID NOs: 1 to 7, respectively, in the part of Summary.

The biotin is used for binding to streptavidin (SA), which is a commonly used technique and has no substantial effect on the effect of the polypeptide in the present invention.

Example 2: Aggregation of Polypeptide in PBS and Solubility of Polypeptide-HSA Complexes Preparation of 10×PBS solution: NaCl 80.00 g, KCl 2 g, $Na_2HPO_4·12H_2O$ 35.8 g or $Na_2HPO_4$ 14.2 g, and $KH_2PO_4$ 2.7 g were added to ultra-pure water to form a volume of 1000 mL, adjusting the pH value thereof to 7.2 to 7.4, and then autoclaving. Preparation of 1×PBS solution: the 10×PBS solution was diluted 10-fold with sterile ultrapure water.

A 1 mg/mL solution of the polypeptide molecules was prepared with sterile ultrapure water and a 125 mg/mL solution of HSA molecules was prepared with sterile ultra-pure water. A certain amount of HSA aqueous solution was added to the aqueous solution of the polypeptide molecules to form a solution in which the molar ratio of polypeptide molecules to HSA molecules is in the range of 4:1 to 1:4. After the solution was well mixed, 1/9 solution volume of 10×PBS solution was added thereto and the solution was diluted to a 1×PBS solution of polypeptide-HSA complex. The prepared solution was placed in a 4° C. refrigerator. A 1×PBS solution only containing polypeptide molecules was used as a control.

At 0 h, the prepared test solution was shaken well, and then 1 mL sample was taken there from by a 1 mL pipette and then transferred into a standard 1 cm×1 cm plastic test sample cell to perform dynamic light scattering (DLS, Zetasizer Nano ZS, Malvern, UK). At 24 h, the solution was shaken well and then subjected to the DLS test. After the test, the solution was placed in a centrifuge (TGL-16B, Anke, China) and was centrifuged at a speed of 5000 rpm for 3 min, the supernatant was sampled and placed into a centrifuge tube, and then the solution in the centrifuge tube was shaken well and then subjected to DLS test. After the test the solution was placed in a 4° C. refrigerator. At 48 h, the solution was shaken well and then subjected to the DLS test. After the test, the solution was centrifuged, and then the supernatant was sampled and placed into a centrifuge tube, and afterwards, the solution in the centrifuge tube was shaken well and then subjected to DLS test. After the test the solution was placed in a 4° C. refrigerator. At 72 h, the solution was shaken well and then subjected to the DLS test. After the test, the solution was centrifuged, and then the supernatant was sampled and placed into a centrifuge tube, and afterwards, the solution in the centrifuge tube was shaken well and then subjected to DLS test.

Dynamic light scattering indicated the change of the particle size of molecules in the solution with time. As shown in FIGS. 1a~1g, particle size of the polypeptide molecules in PBS solution was 300 nm or more at 0 h, and the particle size of the polypeptide molecules in PBS solution would increase significantly in every 24 h. The particle size would decrease significantly after centrifugation, indicating that the polypeptide had the tendency of aggregation in PBS solution. However, The polypeptide-HSA complex was well dispersed in PBS solution, and the particle size did not change greatly within 72 h, and became stable after 72 h, indicating that HSA molecules can significantly increase the solubility of the polypeptide in salt solution.

Example 3: Detection of the Effect of E4-HSA Complex, E5-HSA Complex on Proliferation-Toxicity of SK-BR-3 Cells SK-BR-3 was used as a model system for studying breast cancer cell lines. In a Corning 96-well plate, $1 \times 10^4$ cells were incubated with 100 μL of RPMI-1640 medium (containing 10% fetal bovine serum (FBS) and 1% penicillin-streptomycin) per well and the 96-well plate was pre-incubated under 37° C. and 5% $CO_2$ for 24 hours. 10 μL solutions of poly peptide-HSA complex in PBS at various concentrations were added to the plate so that the final concentrations of the polypeptides were 10 nM, 100 nM, 200 nM, 400 nM, 1 μM, 2 μM, and 4 μM respectively. A blank control was obtained by adding only 10 μL of PBS solution. The culture plate was incubated in an incubator for 48 h, and 10 μL of CCK solution (Beijing FanboBiochemicals Co., Ltd.) was added to each well. The culture plate was incubated for 2 h in the incubator and the absorbance values (OD values) at 450 nm wavelength were measured by a continuous-spectrum multifunctional microplate reader (Tecan infinite M200, TECAN, Switzerland) to calculate cell viability (cell viability=OD450 nm (polypeptide-HSA complex)/(OD450 nm (blank control)×100%).

Figure 2:
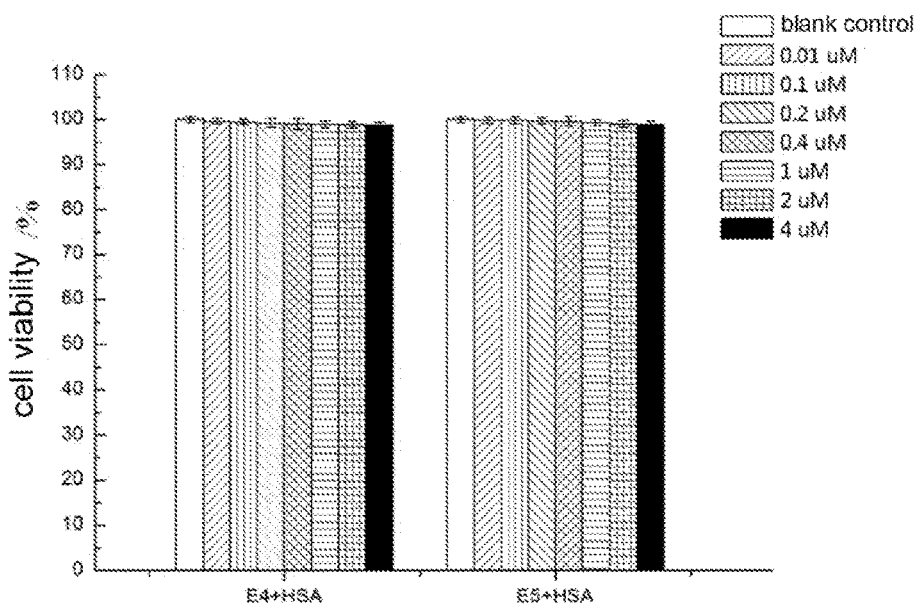
FIG. 2 is a graph showing the experimental results of the effect of the E4-HSA complex and the E5-HSA complex on the viability of SK-BR-3 cells.

In the pre-experiment, the cell viability of SK-BR-3 cells added 4 μM HSA was not significantly different from that of SK-BR-3 cells alone. As shown in FIG. 2, the cell viability of SK-BR-3 cells added 10 nM-4 μM polypeptide-HSA complexes was not significantly different from that of SK- BR-3 cells alone. In such concentration range, the added polypeptide-HSA complex neither promotes cell proliferation nor affects cell viability.

Example 4: Detection of the Effect of E4-HSA Complex, E5-HSA Complex on Proliferation-Toxicity of MDA-MB-231 Cells MDA-MB-231 was used as a model system for studying breast cancer cell lines. In a Corning 96-well plate, $1\times10^4$ cells were incubated with 100 μL of DMEM medium (containing 10% fetal bovine serum (FBS) and 1% penicillin-streptomycin) per well and the 96-well plate was pre-incubated under 37° C. and 5% $CO_2$ for 24 hours. 10 μL of polypeptide-HSA complex in PBS at various concentrations were added to the plate so that the final concentrations of the polypeptides were 10 nM, 100 nM, 400 nM, 1 μM, and 4 μM respectively. A blank control was obtained by adding only 10 μL of PBS solution. The culture plates were incubated in an incubator for 48 h, and 10 μL of CCK solution was added to each well. The culture plates were incubated for 2 h in the incubator and the absorbance values (OD values) at 450 nm wavelength were measured by a continuous-spectrum multifunctional microplate reader to calculate cell viability.

Figure 3:
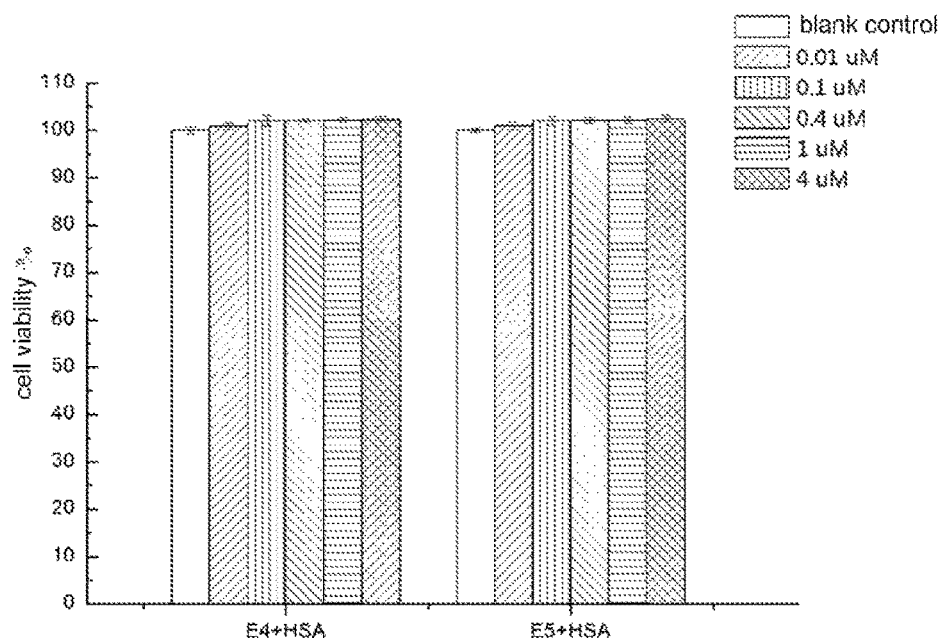
FIG. 3 is a graph showing the experimental results of the effect of the E4-HSA complex and the E5-HSA complex on the viability of MDA-MB-231 cells.

In the pre-experiment, the cell viability of MDA-MB-23 cells added 4 μM HSA was not significantly different from that of MDA-MB-23 cells alone. As shown in FIG. 3, the cell viability of MDA-MB-23 cells added 10 nM-4 μM polypeptide-HSA complexes was not significantly different from that of MDA-MB-23 cells alone. In such concentration range, the added polypeptide-HSA complex neither promotes cell proliferation nor affects cell viability.

Example 5: Inhibitory Effect of E4-HSA Complex and E5-HSA Complex on Lateral Migration of SK-BR-3 Cells Induced by CXCL12

In a Corning 6-well plate, $40\times10^4$ SK-BR-3 cells were incubated with 2 mL of RPMI-1640 medium (containing 10% fetal bovine serum (FBS) and 1% penicillin-streptomycin) per well. The 6-well plate was pre-incubated for 24 h in a 37° C., 5% CO2 incubator. When SK-BR-3 cells were grown to near 90% confluency, 10 μL sterile pipette tips were used to scratch along a straight line in the wells of the plate. Then the cells were gently washed three times with PBS solution. Afterwards, RPMI-1640 medium containing 5% FBS was added to each well and meanwhile the CXCL12 aqueous solution was added to induce the cells, so that the molecule concentration of CXCL12 in each well was 100 ng/mL. Then, the solution of polypeptide-HSA complex in PBS was added so that the final concentration of the polypeptide molecule was 10 nM, 100 nM, and 1000 nM respectively, and PBS solution was added for use as a blank control. The migration of the cells and the change of the scratch width L at 0 h and 24 h after scratching were observed by a microscope with 10× lens (IX71, OLYMPUS, Japan) and the cell migration rate (cell migration rate=polypeptide-HSA complex cell migration rate $(L_{0\ h}-L_{24\ h}/L_{0\ h})$/blank control cell migration rate $(L_{0\ h}-L_{24\ h}/L_{0\ h})\times100\%$) was calculated.

Figure 4A:
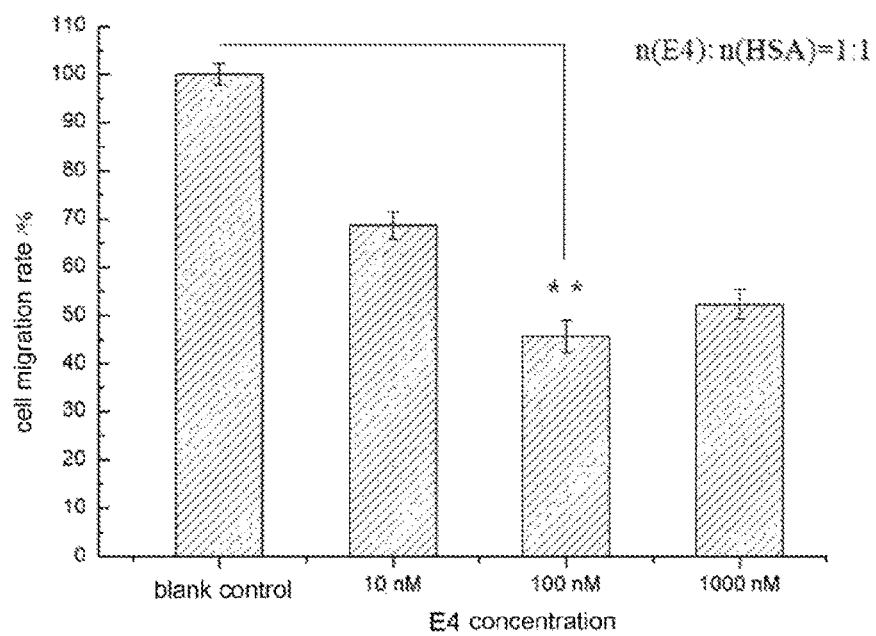
FIGS. 4a-4b are graphs showing the results of the inhibitory effect of the E4-HSA complex and the E5-HSA complex on the lateral migration of SK-BR-3 cells induced by CXCL12.
Figure 4B:
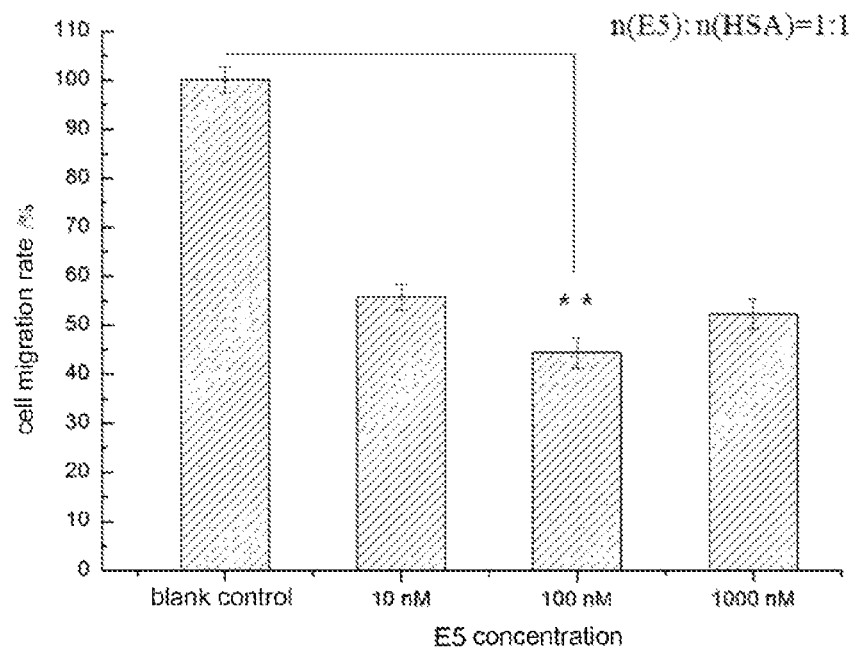
Figure 5A:
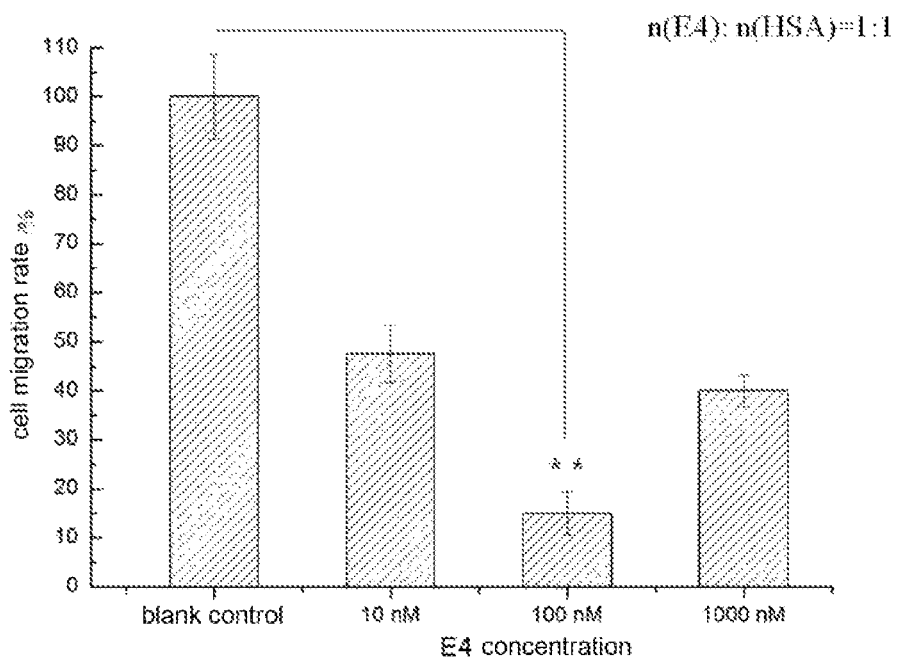
FIGS. 5a-5d are graphs showing the results of the inhibitory effect of the E4-HSA complex and the E5-HSA complex on the longitudinal migration of SK-BR-3 cells induced by CXCL12.
Figure 5B:
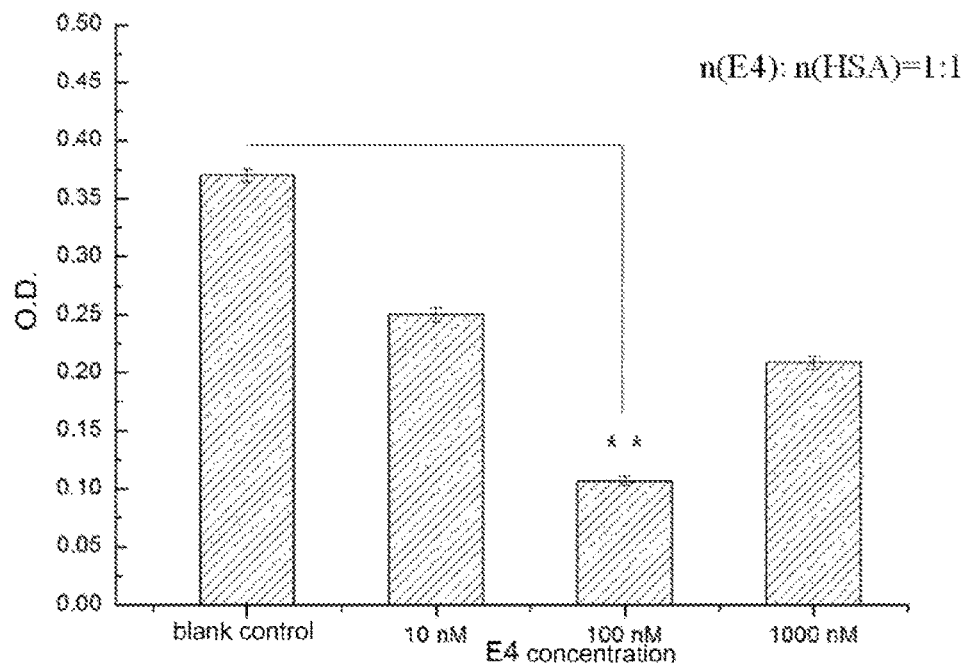
Figure 5C:
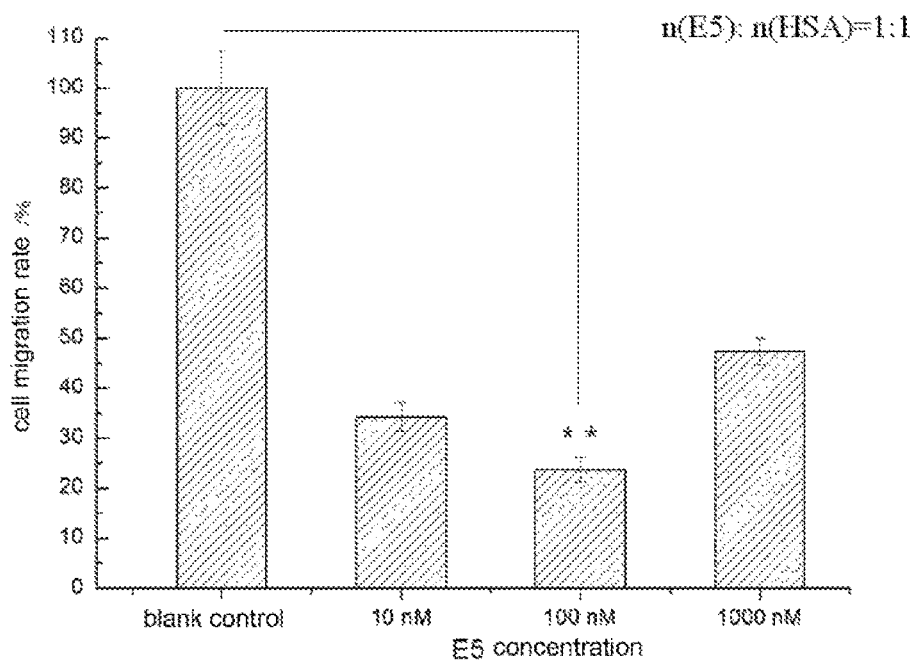
Figure 5D:
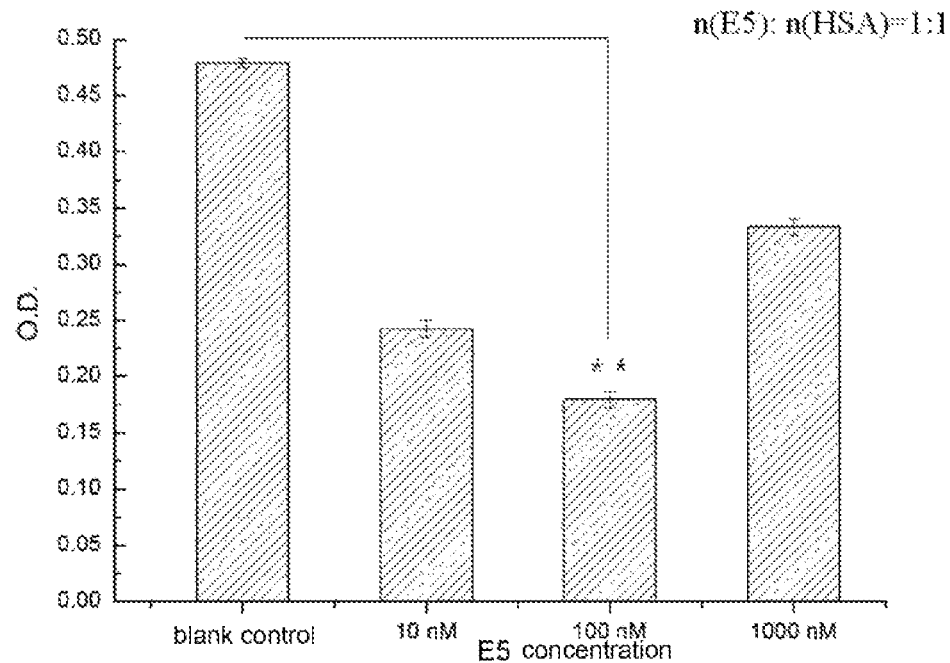

In the pre-experiment, the migration rate of SK-BR-3 cells added 1000 nM of HSA was not significantly different from that of the blank control. As shown in FIGS. 4a-4b, the migration ability of SK-BR-3 cells was decreased by 31.38%, 54.39%, and 47.70% after incubation with 10 nM, 100 nM, and 1000 nM of E4-HSA complexes, respectively. The migration ability of SK-BR-3 cells was decreased by 44.25%, 55.75%, and 47.7% after incubation with 10 nM, 100 nM, and 1000 nM of E5-HSA complexes, respectively. That is to say, polypeptide-HSA complex can effectively inhibit the lateral migration of tumor cells induced by the chemokine CXCL12.

Example 6: Inhibitory Effect of E4-HSA Complex and E5-HSA Complex on Longitudinal Migration of SK-BR-3 Cells Induced by CXCL12

SK-BR-3 cells were harvested in logarithmic growth phase and suspended in RPMI-1640 medium containing 5% FBS. 200 μL of the suspension containing $15\times10^4$ cells and solutions of polypeptide-HSA complex in PBS at different concentrations were added into the upper chamber of a trans well chamber (PET microporous filter membrane with a diameter of 8 μm) so that the final concentration of the polypeptide was 10 nM, 100 nM, and 1000 nM respectively, and PBS solution was added for use as a blank control. 800 μL of RPMI-1640 medium containing 5% FBS was added to the lower chamber (Corning 24-well plate), along with adding the aqueous solution of CXCL12 (100 ng/mL) to induce the cells. The culture plate was incubated in a 37° C., 5% $CO_2$ incubator for 24 h. The trans well chamber was removed and the non-migratory cells on the surface of the upper chamber of the filter membrane were carefully wiped with cotton swabs. The cells migrated through porous membrane in the trans well chamber were fixed and stained with a crystal violet solution (A solution is the solution containing 2 g crystal violet dissolved in 20 mL of 95% alcohol, B solution is the solution containing 0.8 g of ammonium oxalate dissolved in 80 mL of distilled water, A and B are mixed and filtered before use) for 20 min, rinsed with water and then the migrated cells were observed with a 10× microscope (DMI3000B, LEICA, Germany). Five fields in view were taken from each chamber membrane according to the orientation in the upper, lower, left, right and middle directions. The number N of migrated cells in each field of view was counted and the cell migration rate (migration rate=$N_{polypeptide-HSA\ complex}/N_{blank\ control}\times100\%$) was calculated based on the averaged values. Indirectly, the crystal violet was eluted from the stained chamber membrane with 800 μL of 33% acetic acid solution, and 100 μL of the eluate was assayed for OD value at 570 nm using a microplate reader.

In the pre-experiment, migration rate of SK-BR-3 cells added 1000 nM of HSA was compared with that of the blank control, and there was no significant difference in the migration ability of SK-BR-3 cells as calculated by counting the cells on the lower surface of the chamber membrane. As shown in FIGS. 5a-5d, the migration ability of SK-BR-3 cells was decreased by 52.50%, 85.00% and 60.00% after incubation with 10 nM, 100 nM, and 1000 nM of E4-HSA complex, respectively. The measured OD value of the eluted crystal violet was decreased from 0.37 for the control group to 0.25, 0.11 and 0.21. After the cells were incubated with 10 nM, 100 nM and 1000 nM E5-HSA complex respectively, the migration ability of SK-BR-3 cells was decreased by 65.79%, 76.32% and 52.63%, respectively, as calculated by counting the cells migrated through the porous membrane in the trans well chamber. The OD value of the eluate was decreased from 0.48 for the control group to 0.24, 0.18 and 0.33 as indirectly obtained by eluting the crystal violet after staining. That is to say, the polypeptide-HSA complex can effectively inhibit the longitudinal migration of tumor cells induced by chemokine CXCL12.

Example 7: Inhibitory Effect of E4-HSA Complex and E5-HSA Complex on Lateral Migration of MDA-MB-231 Cells Induced by CXCL12

In a Corning 6-well plate, $20\times10^4$ cells were incubated with 2 mL of DMEM medium (containing 10% fetal bovine serum (FBS) and 1% penicillin-streptomycin) per well. The 6-well plate was pre-incubated for 24 h in a 37° C., 5% CO2 incubator. When MDA-MB-231 cells were grown to near 80% confluency, 10 μL sterile pipette tips were used to scratch along a straight line in the wells of the plate. Then the cells were gently washed three times with PBS solution. Afterwards, the serum-free DMEM medium was added to each well and meanwhile the CXCL12 aqueous solution was added to induce the cells, so that the concentration of CXCL12 in each well was 100 ng/mL. Then, the solution of polypeptide-HSA complex in PBS was added so that the final concentration of the polypeptide was 10 nM, 100 nM, and 1000 nM respectively, and PBS solution was added for use as a blank control. The migration of the cells and the change of the scratch width were observed with a microscope at 0 h and 24 h after scratching, and the cell migration rate was calculated.

Figure 6A:
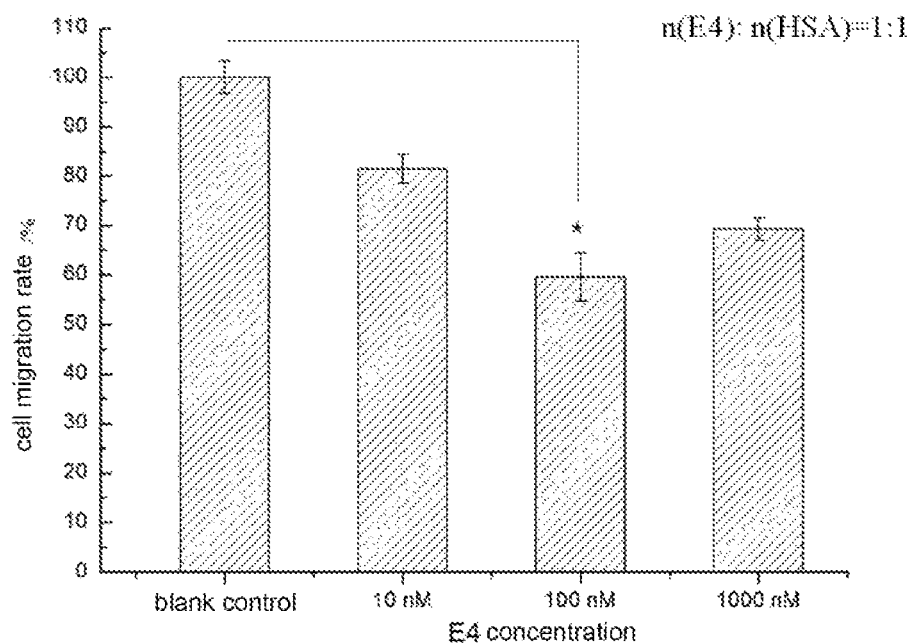
FIGS. 6a-6b are graphs showing the results of the inhibitory effect of the E4-HSA complex and the E5-HSA complex on the lateral migration of MDA-MB-231 cells induced by CXCL12.
Figure 6B:
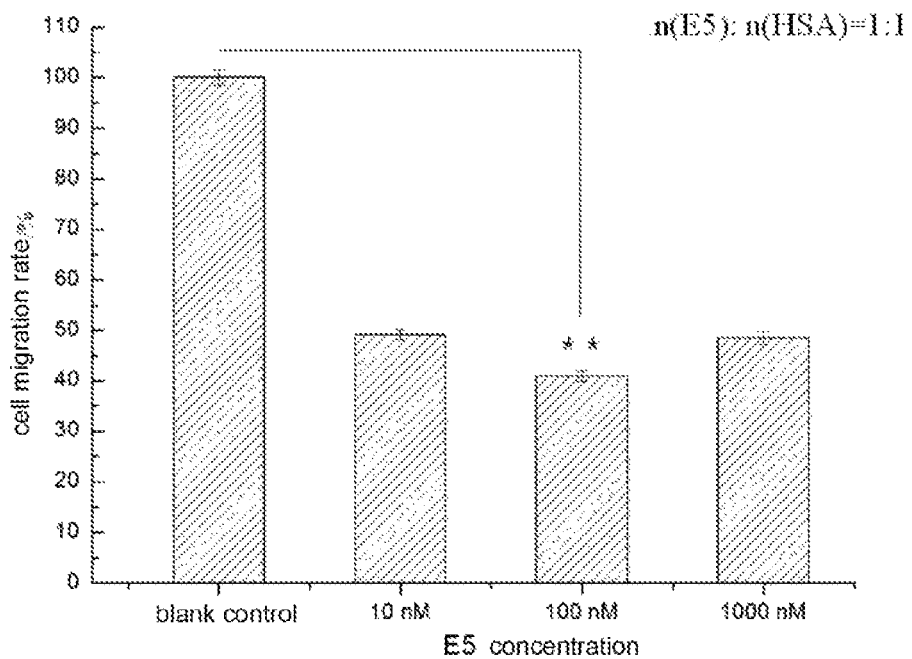
Figure 7A:
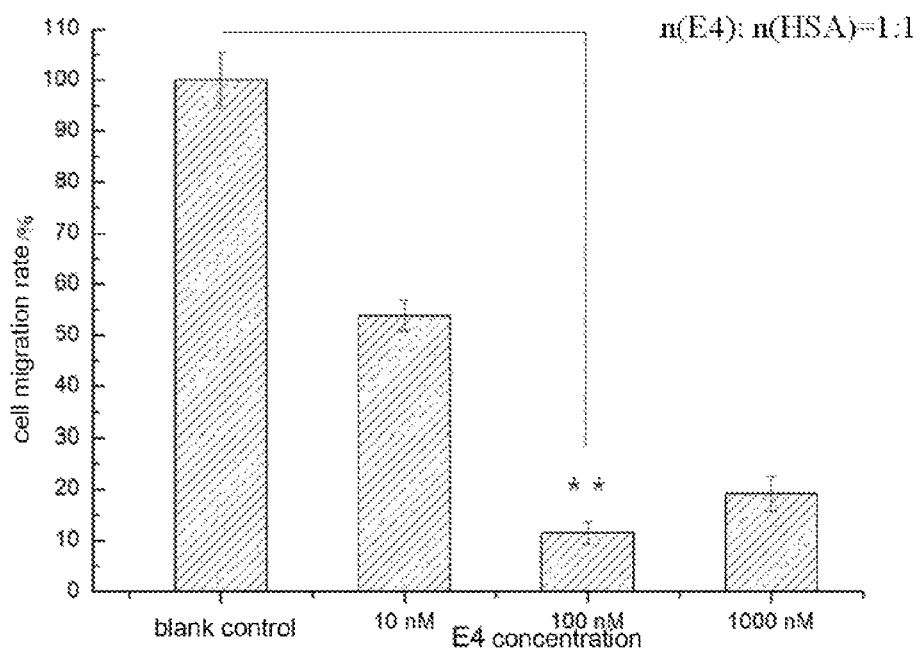
FIGS. 7a-7d are graphs showing the results of the inhibitory effect of the E4-HSA complex and the E5-HSA complex on the longitudinal migration of MDA-MB-231 cells induced by CXCL12.
Figure 7B:
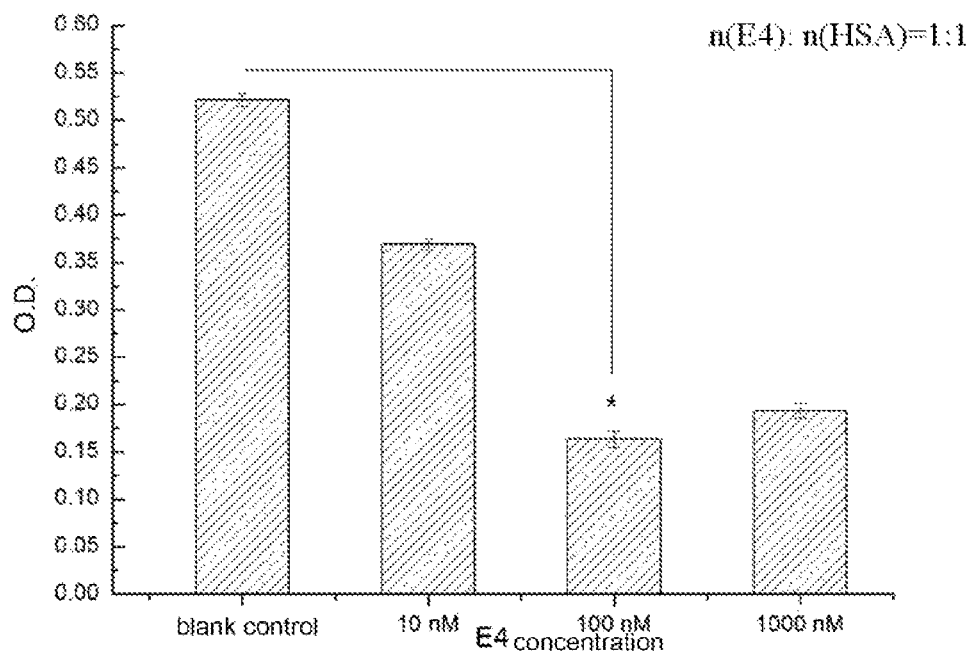
Figure 7C:
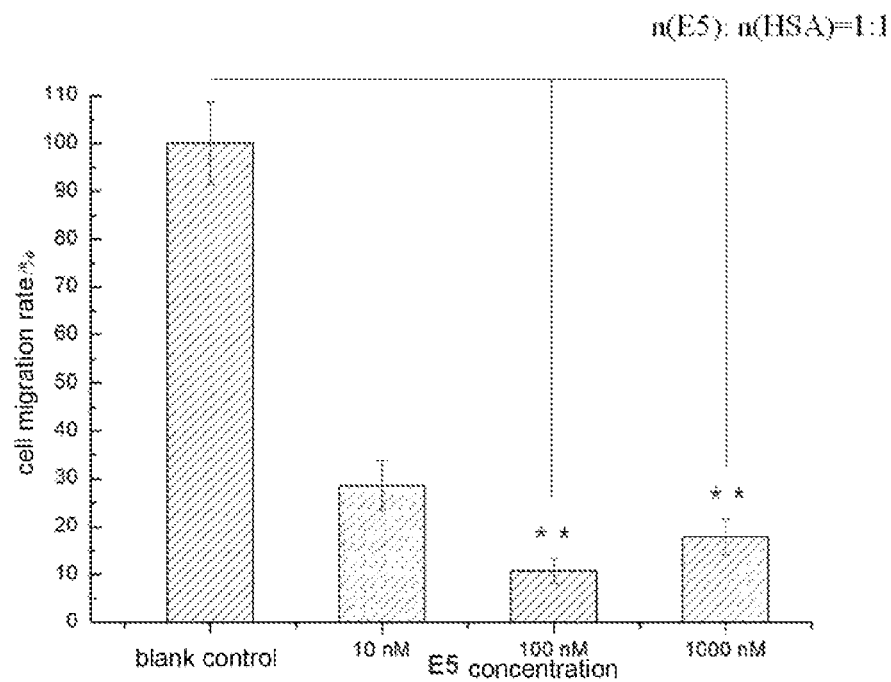
Figure 7D:
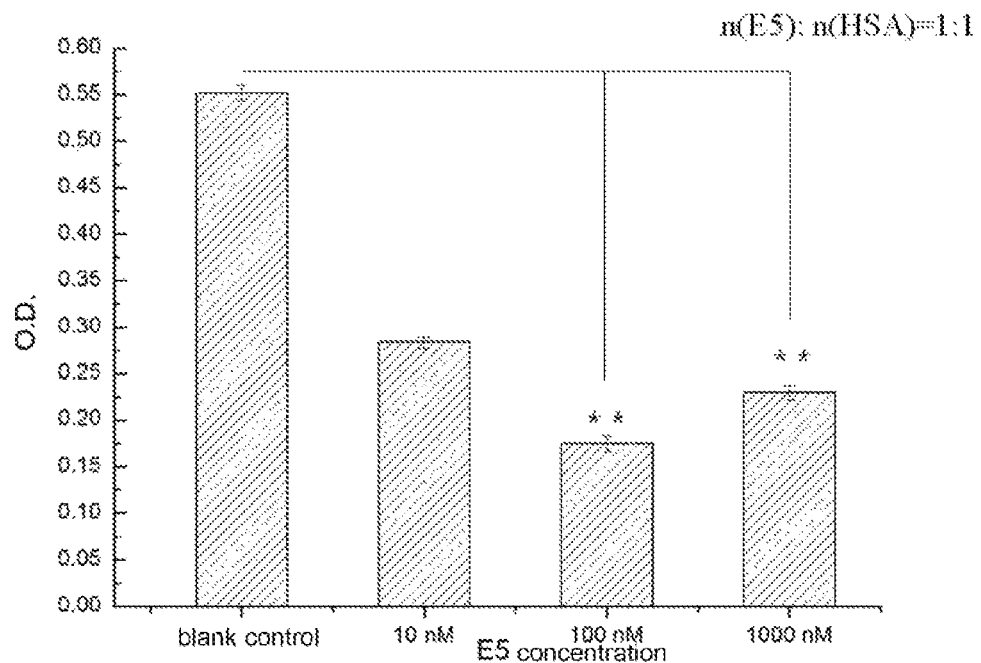

In the pre-experiment, the migration rate of MDA-MB-231 cells added 1000 nM of HSA was not significantly different from that of the blank control. As shown in FIGS. 6a-6b, the migration ability of MDA-MB-231 cells was decreased by 18.54%, 40.49%, and 30.73% after incubation with 10 nM, 100 nM, and 1000 nM of E5-HSA complex, respectively. The migration ability of MDA-MB-231 cells was decreased by 50.87%, 59.09%, and 51.52% after incubation with 10 nM, 100 nM, and 1000 nM of E5-HSA complex, respectively. That is to say, polypeptide-HSA complex can effectively inhibit the lateral migration of tumor cells induced by the chemokine CXCL12.

Example 8: Inhibitory Effect of E4-HSA Complex and E5-HSA Complex on Longitudinal Migration of MDA-MB-231 Cells Induced by CXCL12

MDA-MB-231 cells were harvested in logarithmic growth phase and suspended in serum-free DMEM medium. 200 μL of the suspension containing $10\times10^4$ cells and solutions of polypeptide-HSA complex in PBS at different concentrations were added to the upper chamber of a trans well chamber so that the final concentration of the polypeptide was 10 nM, 100 nM, and 1000 nM respectively, and PBS solution was added for use as a blank control. 800 μL of the serum-free DMEM medium was added to the lower chamber, along with adding an aqueous solution of CXCL12 (100 ng/mL) to induce the cells. The culture plate was incubated in an incubator under 37° C., 5% $CO_2$ for 24 h. The trans well chamber was removed and the non-migratory cells on the surface of the upper chamber of the filter membrane were carefully wiped with cotton swabs. The cells migrated to the lower surface of the chamber membrane were fixed and stained with a crystal violet solution, rinsed with water and then the migrated cells were observed with a microscope. Five fields in view were taken for each chamber membrane according to the orientation in the upper, lower, left, right and middle directions. The number of migrated cells in each field of view was counted and the cell migration rate was calculated based on the averaged values. Indirectly, the crystal violet was eluted from the stained chamber membrane with 800 μL of 33% acetic acid solution, and 100 μL of the eluate was assayed for OD value at 570 nm using a microplate reader.

In the pre-experiment, the migration rate of MDA-MB-231 cells added 1000 nM of HSA was not significantly different from that of the blank control. As shown in FIGS. 7a-7d, the migration ability of MDA-MB-231 cells was decreased by 46.15%, 88.46% and 80.77% after incubation with 10 nM, 100 nM, and 1000 nM of E4-HSA complex, respectively, as obtained by counting the cells migrated through the porous membrane in the trans well chamber, and the OD value of the eluate was decreased from 0.52 for the control group to 0.37, 0.16 and 0.19 as indirectly obtained by eluting the crystal violet after staining. After the cells were incubated with 10 nM, 100 nM and 1000 nM E5-HSA complex respectively, the migration ability of MDA-MB-231 cells was decreased by 71.43%, 89.29%, and 82.14%, respectively, as calculated by counting the cells on the lower surface of the chamber membrane. The OD value of the eluate was decreased from 0.55 for the control group to 0.28, 0.17 and 0.23 respectively as indirectly obtained by eluting the crystal violet after staining. That is to say, the polypeptide-HSA complex can effectively inhibit the longitudinal migration of tumor cells induced by chemokine CXCL12.

Example 9: Inhibitory Effect of E5 on Longitudinal Migration of Leukemic Cells HL-60 and U937 Cells Induced by CXCL12

HL-60 and U937 cells were harvested in logarithmic growth phase and suspended in RPMI-1640 medium without FBS. 200 μL of the suspension containing $20\times10^4$ cells and aqueous solutions of E5 at different concentrations were added to the upper chamber of a trans well chamber (PET microporous filter membrane with a diameter of 80 μm was used for HL-60, and PET microporous filter membrane with a diameter of 5 μm was used for U937) so that the final concentration of the polypeptide molecule was 0.1 μM, 1.0 μM, and 10 μM respectively, and an aqueous solution was added for use as a blank control. 800 μL of the RPMI-1640 medium without FBS was added to the lower chamber, along with adding aqueous solutions of CXCL12 at concentrations of 200 ng/mL and 50 ng/mL respectively to induce HL-60 and U937 cells. The culture plates were incubated in an incubator under 37° C., 5% $CO_2$ for 24 h. The trans well chambers were removed and the number of the migrated cells in the lower chamber was calculated.

Figure 8:
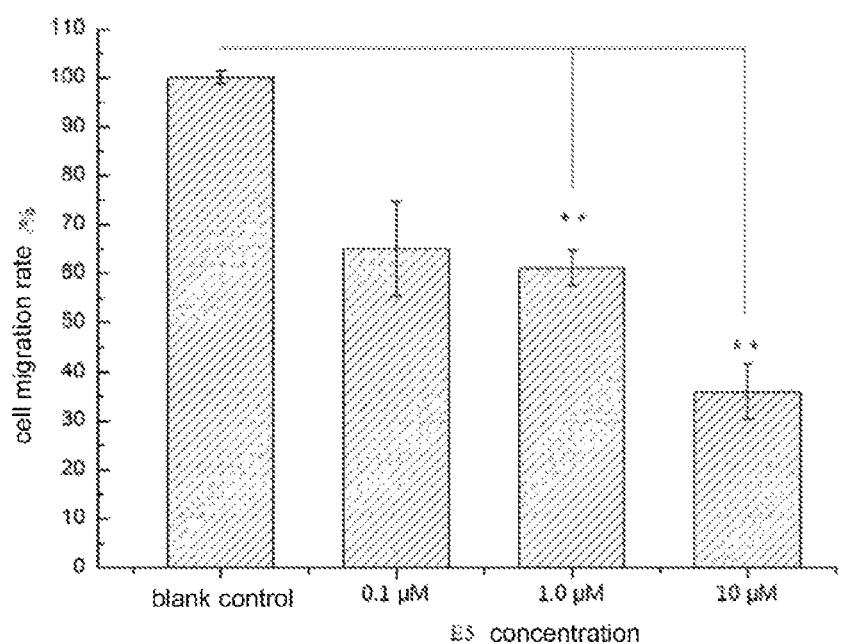
FIG. 8 is a graph showing the results of the inhibitory effect of E5 on the longitudinal migration of HL-60 cells induced by CXCL12.
Figure 9:
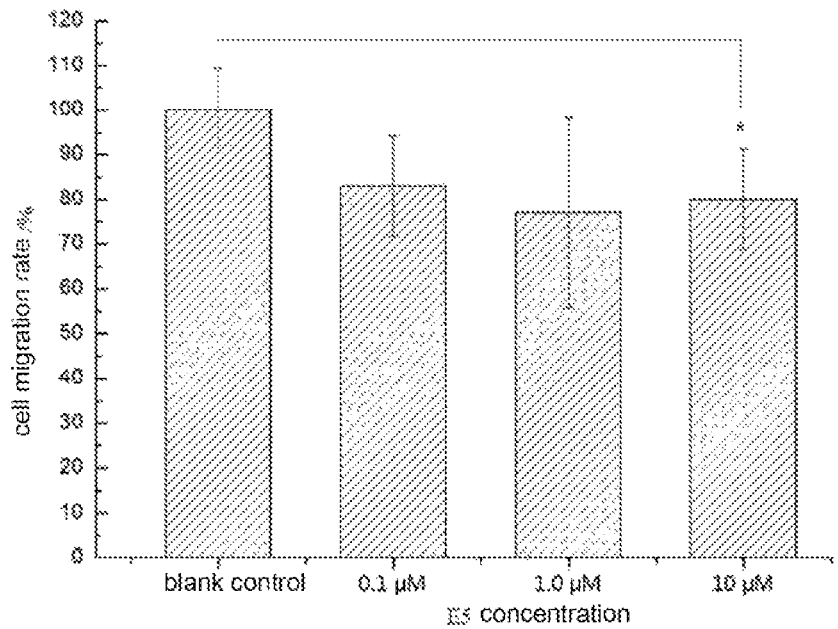
FIG. 9 is a graph showing the results of the inhibitory effect of E5 on the longitudinal migration of U937 cells induced by CXCL12.

As shown in FIG. 8, the migration ability of HL-60 cells was decreased by 35.00%, 39.00%, and 64.00% after incubation with 0.1 μM, 1.0 μM, and 10 μM of E5, respectively, as obtained by calculating the number of the cells in the lower chamber. That is to say, E5 can effectively inhibit the longitudinal migration of leukemic cells HL-60 cells induced by chemokine CXCL12. As shown in FIG. 9, the migration ability of U937 cells was decreased by 17.00%, 23.00%, and 20.00% after incubation with 0.1 μM, 1.0 μM, and 10 μM of E5, respectively, as obtained by calculating the number of the cells in the lower chamber. That is to say, E5 can effectively inhibit the longitudinal migration of leukemic cells U937 cells induced by chemokine CXCL12. The results in FIGS. 8 and 9 showed that the polypeptide can effectively inhibit migration of leukemic cells.

Example 10: Inhibitory Effect of E4-HSA Complex and E5-HSA Complex on Longitudinal Migration of HL-60 Cells Induced by CXCL12

HL-60 cells were harvested in logarithmic growth phase and suspended in RPMI-1640 medium without FBS. 200 μL of the suspension containing 20×10⁴ cells and solutions of polypeptide-HSA complex in PBS at different concentrations were added to the upper chamber of a trans well chamber so that the final concentration of the polypeptide was 10 nM, 100 nM, and 1000 nM respectively, and PBS solution was added for use as a blank control. 800 µL of the RPMI-1640 medium without FBS was added to the lower chamber, along with adding aqueous solutions of CXCL12 (200 ng/mL) to induce the cells. The culture plates were incubated in a 37° C., 5% CO2 incubator for 24 h. The trans well chambers were removed and the number of the migrated cells in the lower chamber was calculated.

Figure 10A:
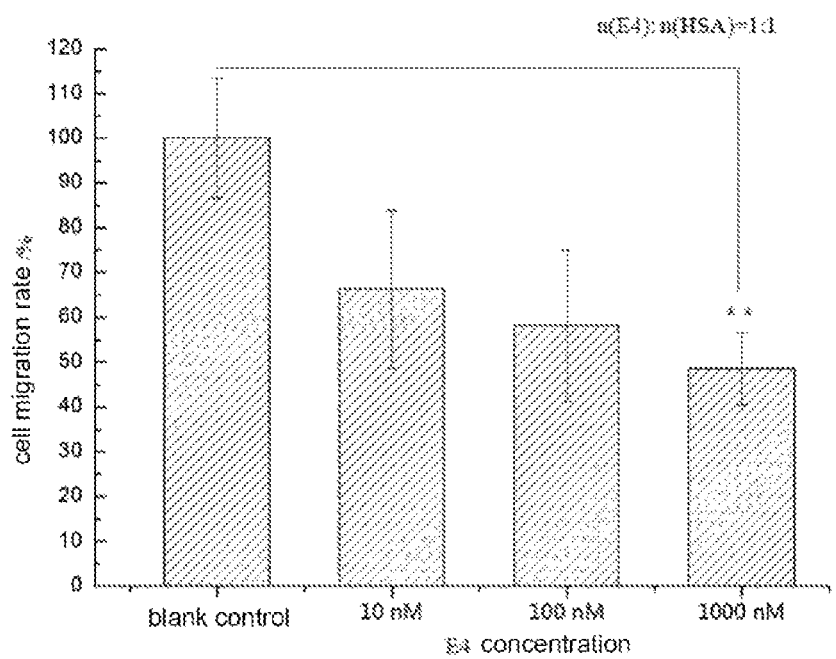
FIGS. 10a-10b are graphs showing the results of the inhibitory effect of the E4-HSA complex and the E5-HSA complex on longitudinal migration of HL-60 cells induced by CXCL12.
Figure 10B:
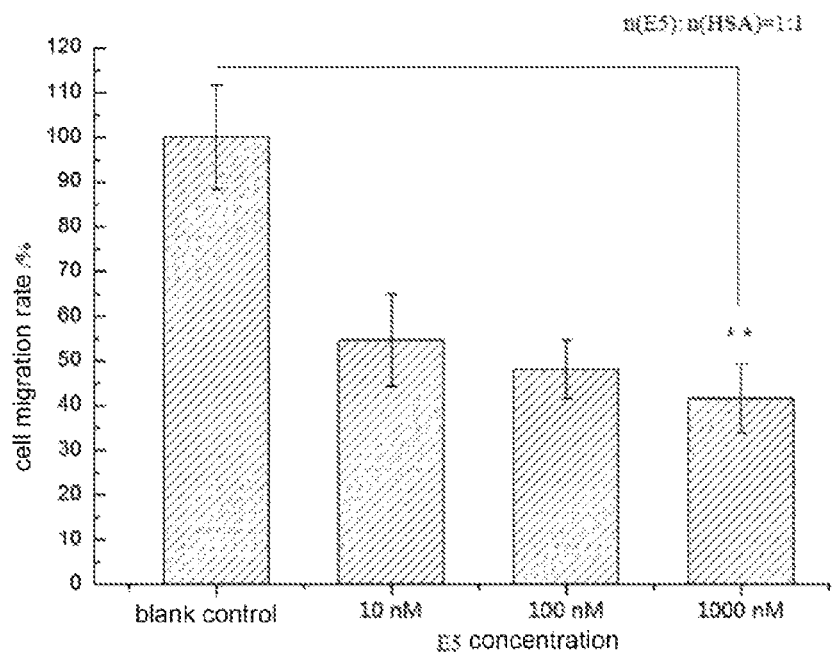

In the pre-experiment, the migration rate of HL-60 cells added 1000 nM of HSA was not significantly different from that of the blank control. As shown in FIGS. 10a-10b, the migration ability of HL-60 cells was decreased by 33.78%, 41.89%, and 51.35% after incubation with 10 nM, 100 nM, and 1000 nM of E4-HSA, respectively, as obtained by calculating the number of the cells in the lower chamber. The migration ability of HL-60 cells was decreased by 45.46%, 51.95%, and 58.44% after incubation with 10 nM, 100 nM, and 1000 nM of E5-HSA complex, respectively, as obtained by calculating the number of the cells in the lower chamber. That is to say, polypeptide-HSA complex can more effectively inhibit the longitudinal migration of leukemic cells induced by chemokine CXCL12.

Example 12: Effect of E5 on CXCL12-Induced Apoptosis of Leukemia Cells HL-60 and U937 Cells The effect of E5 polypeptide on the apoptosis of leukemia cells HL-60 and U937 cells was examined by FITC-Annexin V/PI (eBioscience, Australia) double-staining assay. HL-60 and U937 cells were harvested in logarithmic growth phase. The cell suspensions and E5 aqueous solutions at different concentrations were added to 24-well plates. After incubation for 24 h, the cells were collected and washed with PBS. FITC-Annexin V and PI were added after the cells were resuspended in a binding buffer (10 mM Hepes/NaOH, pH 7.4, 140 mM NaCl, 2.5 mM $CaCl_2$). After incubating for 10 min at room temperature, 1.5×10⁴ cells were analyzed by flow cytometer (Accuri C6, BD, USA).

Figure 11A:
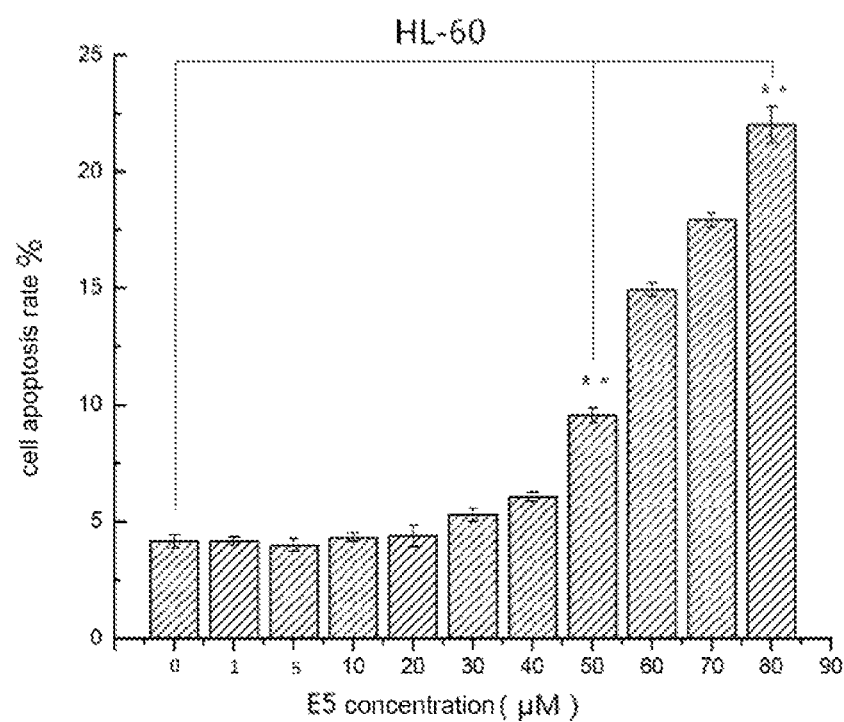
FIGS. 11a-11b are graphs showing the results of the effect of E5 on apoptosis of HL-60 and U937 cells.
Figure 11B:
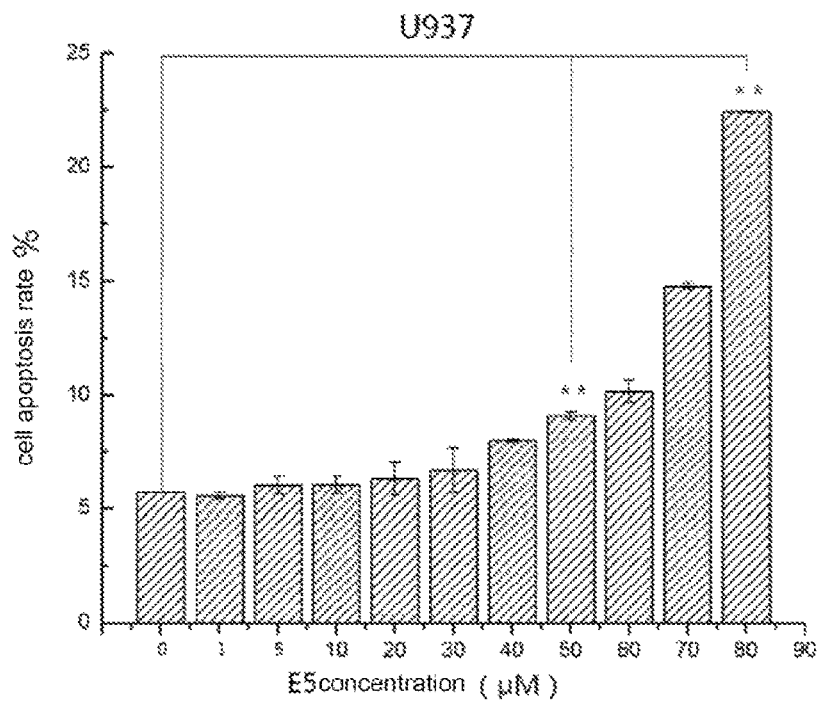

As shown in FIGS. 11a-11b, when the concentration of E5 was below 20 µM, the effect of E5 on apoptosis of leukemia cells HL-60 and U937 cells was negligible, but when the concentration of E5 was higher than 20 µM, the apoptosis rate of leukemia cells was increased rapidly. When the concentration of E5 was 50 µM, the apoptosis rate of leukemia cells was increased to 10%. When the concentration of E5 reached to 80 µM, the apoptosis rate of leukemia cells was increased to 22%. That is to say, E5 at high concentrations can cause apoptosis of leukemia cells and kill leukemia cells.

Example 13: In Vivo Experiments of E5 Prolonging the Survival of Mice Transplanted with Leukemic Cells The 5-week-old female NOD/SCID mice (purchased from the Animal Experimental Center of the Institute of Basic Medical Science, Chinese Academy of Medical Sciences) cultured in a special sterile environment were used. Prior to the experiment, animals should be acclimated to the laboratory environment for 1 week. 1×10⁶ HL-60 cells were suspended in 100 µL ethylene diamine tetraacetic acid sodium (EDTA)/PBS and injected intravenously into NOD/SCID mice subjected to sub-lethal irradiation (250 cGy). 18 days after cell transplantation, compared with the blank control group, the transplanted mice showed apparently leukemia symptoms, such as hind limb paralysis, fur wrinkling, arched posture, and so on. From day 20 after transplantation, the mice were injected with E5 (30 mg/kg, n=9), cyclophosphamide (CTX, 36 mg/kg, n=9), or sterile water (n=8) respectively twice a week to observe the state and weight changes of the mice, wherein E5 and sterile water were injected into mice by subcutaneous injection and cyclophosphamide was injected into mice by intraperitoneal injection.

Figure 12A:
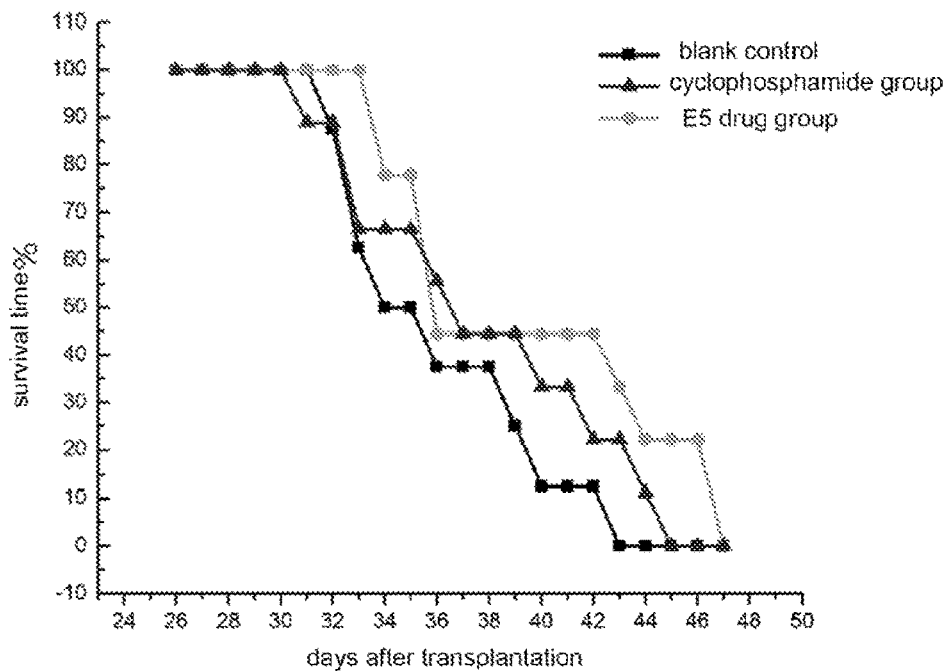
FIGS. 12a-12b are graphs showing the in vivo experimental results of the effect of E5 for prolonging survival time of mice transplanted with leukemic cells.
Figure 12B:
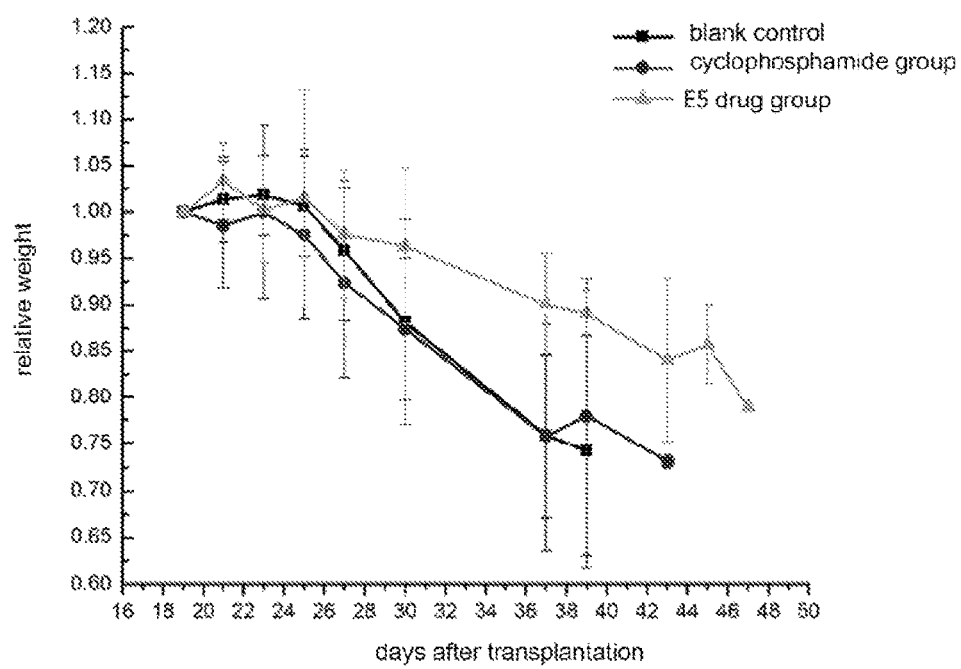

As shown in FIG. 12a, mice in the E5-treated group showed longer survival time than the cyclophosphamide group and the control group, and E5 showed a better therapeutic effect on leukemia compared with the cyclophosphamide drug. As shown in FIG. 12b, the weight of mice transplanted with the cells in the E5-treated group was much higher than that in the cyclophosphamide group and the control group, indicating that E5 could prolong the survival time of mice transplanted with leukemia cells while inhibiting the loss of weight.

The above experiments show that the polypeptide-human serum albumin (HSA) complex of the present invention has better solubility in a salt solution as compared to the polypeptide alone, and both the polypeptide and polypeptide-HSA complex have effects of inhibiting tumor metastasis and treating leukemia, which can provide a feasible method for inhibiting tumor metastasis and treating leukemia.

The applicant declares that the present invention is described by way of the above-described embodiments, but the present invention is not limited to the above-described process steps, and does not mean that the present invention must be carried out in dependence on the above-mentioned process steps. It should be apparent to those skilled in the art that any modifications of the invention, equivalents of the materials selected for the invention, addition of auxiliary components, selection of specific modes, etc., fall within the protection scope and disclosure scope of the present invention.

The invention claimed is:

1. A polypeptide for inhibiting tumor cell metastasis and treating leukemia, wherein the polypeptide has the amino acid sequence of SEQ ID NO: 3.

2. A polypeptide-human serum albumin complex comprising the polypeptide according to claim 1 and human serum albumin.

* * * * *